United States Patent
Brewer et al.

(10) Patent No.: US 8,544,463 B2
(45) Date of Patent: Oct. 1, 2013

(54) OVERMOLDED MANIFOLD O-RING

(75) Inventors: John Brewer, Marietta, GA (US);
Cassandra E. Morris, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 531 days.

(21) Appl. No.: 12/891,957

(22) Filed: Sep. 28, 2010

(65) Prior Publication Data
US 2012/0073575 A1  Mar. 29, 2012

(51) Int. Cl.
*A61M 39/00* (2006.01)
*A61M 16/00* (2006.01)

(52) U.S. Cl.
USPC .................................................. 128/200.24

(58) Field of Classification Search
USPC ............ 128/200.24, 200.26, 205.24, 207.14, 128/207.15; 604/319, 540
See application file for complete search history.

(56) References Cited

U.S. PATENT DOCUMENTS

| | | | |
|---|---|---|---|
| 5,735,271 A * | 4/1998 | Lorenzen et al. | 128/207.16 |
| 7,779,842 B1 * | 8/2010 | Russo | 128/207.14 |
| 2010/0147310 A1 | 6/2010 | Brewer | |

FOREIGN PATENT DOCUMENTS

| | | |
|---|---|---|
| DE | 195 08 509 A1 | 9/1996 |
| DE | 10 2005 01534 A1 | 10/2006 |
| EP | 0 583 599 A1 | 2/1994 |
| WO | WO 9919013 A1 * | 4/1999 |

* cited by examiner

*Primary Examiner* — Justine Yu
*Assistant Examiner* — Timothy Stanis
(74) *Attorney, Agent, or Firm* — James B. Robinson

(57) ABSTRACT

A respiratory access assembly includes a distal plate having one port and cuff and an axially aligned proximal plate including a first port and first cuff and a second port and second cuff. The distal plate is configured to move relative to the proximal plate. The respiratory access assembly includes an actuator, which has a plurality of predetermined positions. The actuator includes a blocking portion that controls the movement of the plates. The blocking portion moves slidably within an O-ring that prevents loss of pressure from the artificial airway system. The O-ring may be molded in place using an injection molding process, thus ensuring good adhesion to the disk.

3 Claims, 10 Drawing Sheets

OVERMOLDED MANIFOLD O-RING

The disclosures herein relate generally to improved medical care for intubated patients, and more particularly to an improved sealing system for multiple access respiratory ports for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern.

For example, in low lung capacity patients, such as premature babies and adults suffering from emphysema, one problem is the removal of accumulated lung secretions. It is undesirable to starve such patients of oxygen during the secretion removal process. Secretion removal is accomplished via a suction catheter which is temporarily positioned via a respiratory access assembly in an artificial airway, i.e., an endotracheal tube placed in a portion of the patient's respiratory tract to provide air (oxygen and other gases) to the lungs of such patients.

With these and other patients undergoing respiratory care while intubated, problems may occur, including problems with a respiratory access assembly. Unsafe extended use of a respiratory access assembly for ventilating, aspirating, suctioning and other functions may result in hospital acquired infections, such as, for example, ventilator acquired pneumonia. Also of concern is the reliability of such respiratory access assemblies. Further, the need to open the ventilator circuit to exchange devices and perform other therapeutic treatments is also a concern.

A respiratory access assembly needs to be quickly and easily removed and exchanged without compromising the quality of health care to the patient. Also of concern with a respiratory access assembly is inadvertent conversion from a closed respiratory system to an open respiratory system via malfunction of a respiratory access assembly. Therefore, it would be desirable to have an easy to operate, fail-safe, closed-system respiratory access assembly which provides safe and predictable closed-system access to an intubated patient's respiratory system for multiple purposes, and which has safety features to reduce or eliminate inadvertent damage of the closed respiratory system.

The present disclosure addresses the need for a respiratory access assembly that has better sealing properties than those available previously and is also simpler to assemble. Access to the closed respiratory system through one or more access sites is provided, for example, to ventilate the lungs of the patient with gas or gases, to aspirate secretions from the lungs, to oxygenate the lungs to eliminate or reduce residual carbon dioxide, to visually inspect selected parts of the patient's respiratory system, to sample sputum and gases, to sense parameters such as flow rates, pressure, and/or temperature, to flush with solution(s), and to administer medication, gases, and/or to lavage.

SUMMARY OF THE DISCLOSURE

In response to the difficulties and problems discussed herein, a respiratory access assembly is provided. The respiratory access assembly comprises a distal plate having a port. The port is adapted to be positioned in operable communication with an artificial airway of a patient. The assembly also includes a proximal plate. The proximal plate has a first port and a second port. The distal plate is positioned against the proximal plate in a stacked configuration. Each plate is configured to move. In addition, the assembly includes an actuator positioned adjacent to at least one plate. The actuator cooperates with at least one plate to permit movement of at least one plate when the actuator is positioned in a movement-enabling position. The actuator cooperates with both plates to lock the plates in a fixed position when the actuator is positioned in a locked position, such that the plates are locked into a predetermined position relative to each other. The actuator includes a blocking portion which is configured to extend into at least one port when the actuator is positioned in the movement-enabling position, and to withdraw from the one port when the actuator is positioned in the locked position.

LIST OF REFERENCE NUMBERS

Figure 1:
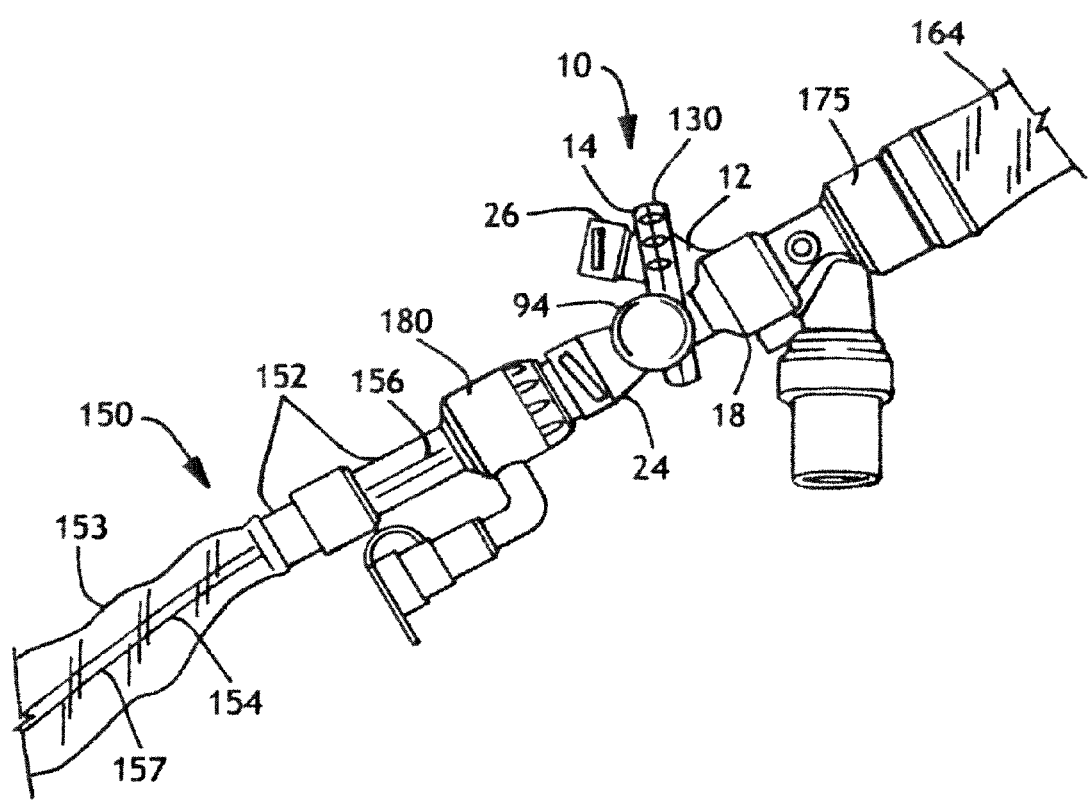
FIG. 1 is a perspective view of the respiratory access assembly of the present disclosure illustrating the assembly in use and coupled to a respiratory manifold which is attached to an endotracheal tube at a distal end of the assembly, a filter and a suction catheter assembly coupled to a proximal end of the assembly.

10 Pod Assembly
12 Distal Plate
14 Proximal Plate
16 Angled Port
18 Angled Cuff
20 First Port
22 Second Port
24 Second Cuff
26 Second Cuff
28 Lip
30 Outer Edge
31 First Notch
32 Second Notch
34 Ramps
40 Proximal Surface
42 Junction
43 Inner Periphery
44 Rib
48 Seal
50 Perimeter
54 Distal Surface
56 Proximal Surface
58 Perimeter Rib
62 Opening
64 Port Rib
66 Distal Surface
70 Outer Edge
72 Outer Lip
74 Two Notches
76 Inner Rib
79 Inner Periphery
80 Rotating Groove
81 Tab
82 First Perimeter Rib
83 Second Perimeter Rib
85 Small Channel
86 Channel
88 Opening
90 Button Housing
91 Button Assembly
92 Plunger
94 Button
96 Proximal Surface
99 Divot
100 Side Opening
101 Flange
102 O-ring
104 Spring
106 Thumb Landing Area
108 Outer Shell
110 Inner Shell
113 Perimeter Edge
114 Holding Tab
116 Locking Tab
118 Movement-Permitting Portion
130 Round Collar
132 Thumb Landing
134 Outer Perimeter Surface
136 Plurality of Ribs
138 Cut-away Portion
140 Inner Surface
150 Suction Catheter Assembly
152 Distal End Connector
153 Sleeve
154 Suction Catheter
156 Distal Tip
157 Elongated Body
164 Artificial Airway
165 Axis
172 First Direction
173 Second direction

DETAILED DESCRIPTION OF THE DISCLOSURE

Suction catheters are well known and widely commercially available for many medical uses. Suctioning may be performed using an "open" or "closed" system. In the open system, the suction catheter is merely a flexible plastic tube that is inserted into the flexible lumen with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the tradename TRACH CARE® from Kimberly-Clark Corporation (formerly BALLARD® Medical Products).

As the patient requires artificial removal of secretions, the closed suction catheter may be advanced through one end of the plastic bag, through a connecting fitting and into the flexible lumen. The other (proximal) end of the suction catheter is attached to a source of suction. Suction may be applied using, for example, a finger controlled valve on the proximal end of the suction catheter, and the secretions removed. Secretions are thus drawn into the lumen of the suction catheter tube and removed and the system remains closed.

The suction catheter is subsequently withdrawn from the flexile lumen and back into the plastic bag to keep the circuit closed. Closed suction systems are generally preferred by healthcare providers since the provider is better protected from the patient's secretions. Closed suction systems are also easier and quicker to use since a sterile field does not need to be created each time the patient must be suctioned, as is required in open suction systems. The closed suction catheter may be permanently attached to the proximal end of the flexible lumen or may be detachably connected so that it may be replaced periodically.

Many current designs for respiratory access assemblies may have only one port. In these instances, the suction catheter must be removed when other tasks need to be performed, such as, for example, bronchoscopy, bronchial alveolar lavage, and so forth. Opening a closed ventilating system by removing the suction catheter on such a ventilated patient can lead to infection, as noted previously. Also, current designs of multiple access port manifolds and/or assemblies do not contain a safety lock. In certain instances, due to the lack of such a safety lock, the introduction of a suction catheter through a manifold port may result in a portion of the catheter being cut off and aspirated into the patient's lungs. This can lead to significant complications, including airway blockage, infection, and even death. Failure to adequately seal a respiratory access assembly may cause a compromise of positive end-expiration pressure (PEEP), which in turn may cause suboptimal ventilation which can result in collapsing alveoli in the patient's lungs.

The present disclosure describes a respiratory access assembly which includes features which permits multiple access without opening the closed ventilation system, and it contains a safety lock feature which prevents loss of any portion of the suction catheter and contains an improved sealing feature.

The embodiments illustrated and described herein provide three assemblies which are substantially similar. The first and second assemblies describe and illustrate stacked and aligned disks. The third embodiment describes and illustrates stacked and aligned plates. All three embodiments are intended as non-limiting examples.

Figure 10A:
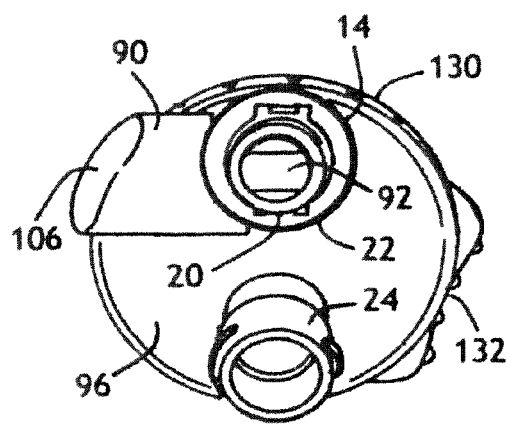
FIG. 10A is a plan view of the proximal surface of the proximal disk of FIGS. 1, 2, 4 and 6, but showing the button in a pressed-in (movement-enabling) position, a plunger of the button blocking a first port.
Figure 10B:
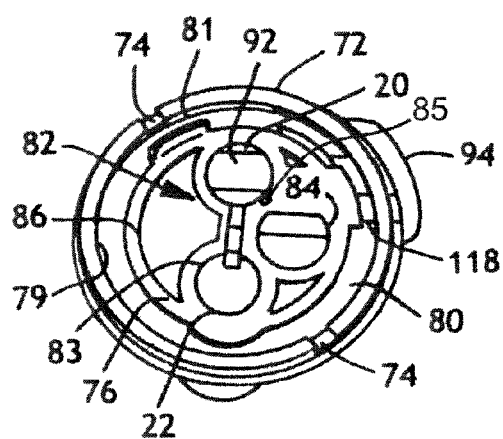
FIG. 10B is a plan view of the distal surface of the proximal disk of FIG. 10A.
Figure 10C:
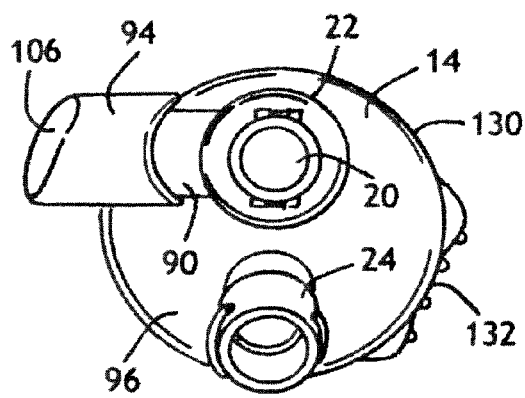
FIG. 10C is a plan view of the proximal surface of the proximal disk of FIG. 10A, but shown the button in a moved out (locked) position, the plunger moved out of the first port.
Figure 10D:
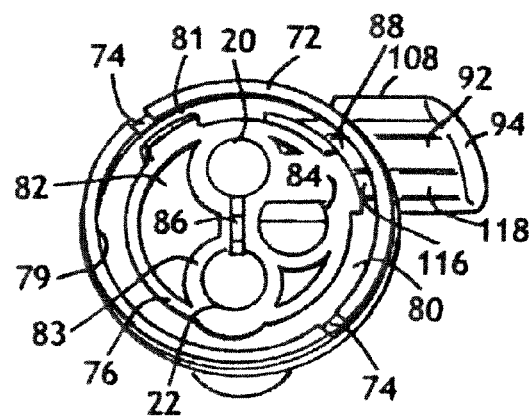
FIG. 10D is a plan view of the distal surface of the proximal disk of FIG. 10D.
Figure 11:
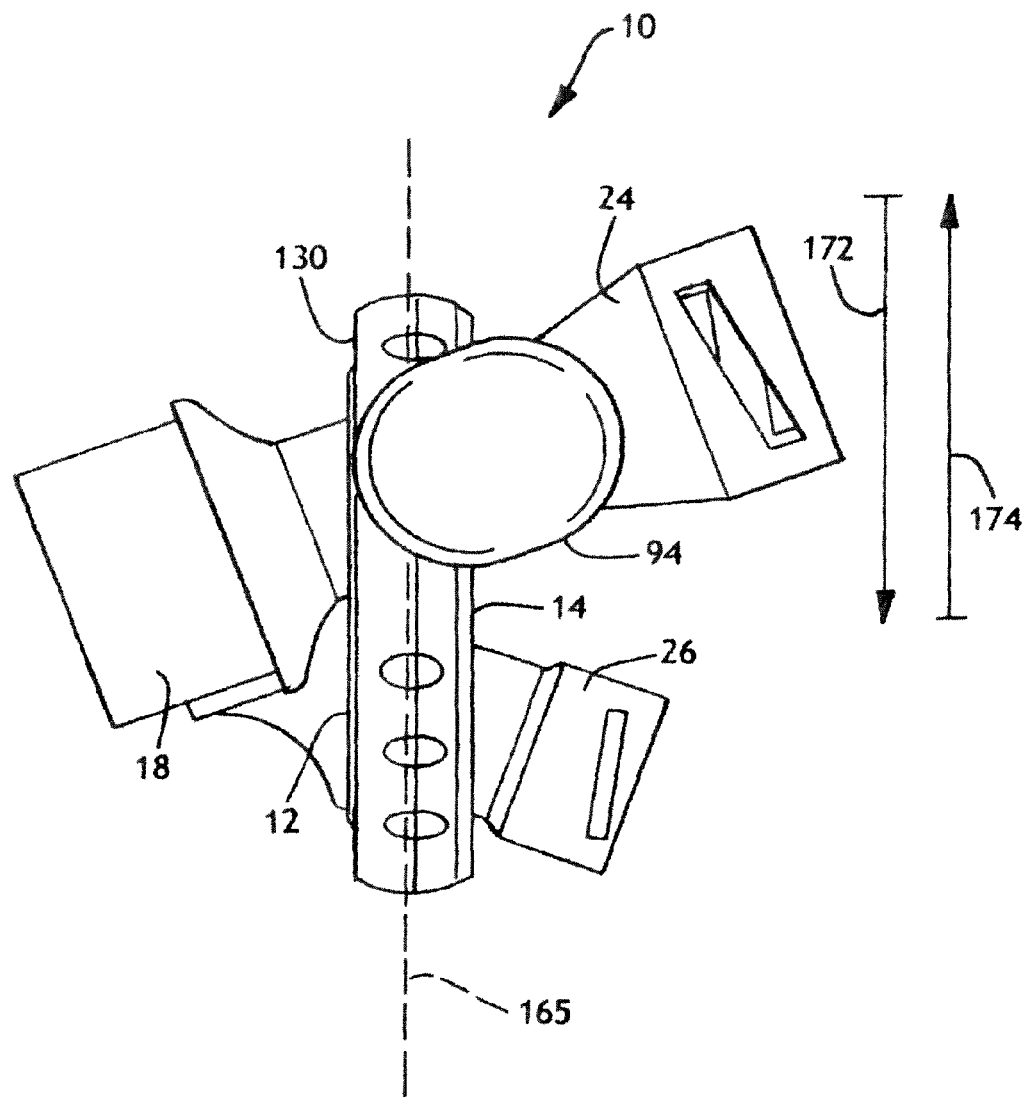
FIG. 11 is a side view of the respiratory access assembly of the present disclosure, showing the port of the distal disk in an axial alignment with the first port of the proximal disk in an open position (first open position)
Figure 12:
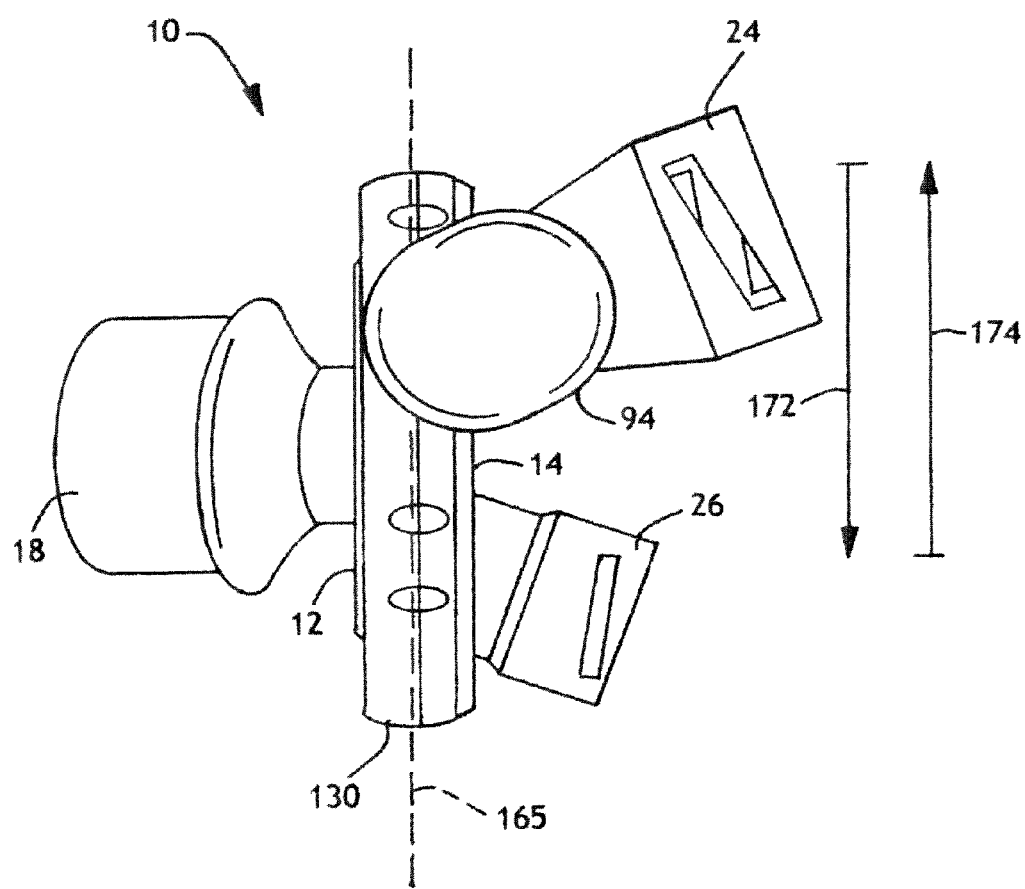
FIG. 12 is a side view of the respiratory access assembly of the present disclosure, showing the port of the distal disk positioned between the first port and the second port of the proximal disk in a closed position (all ports closed)
Figure 13:
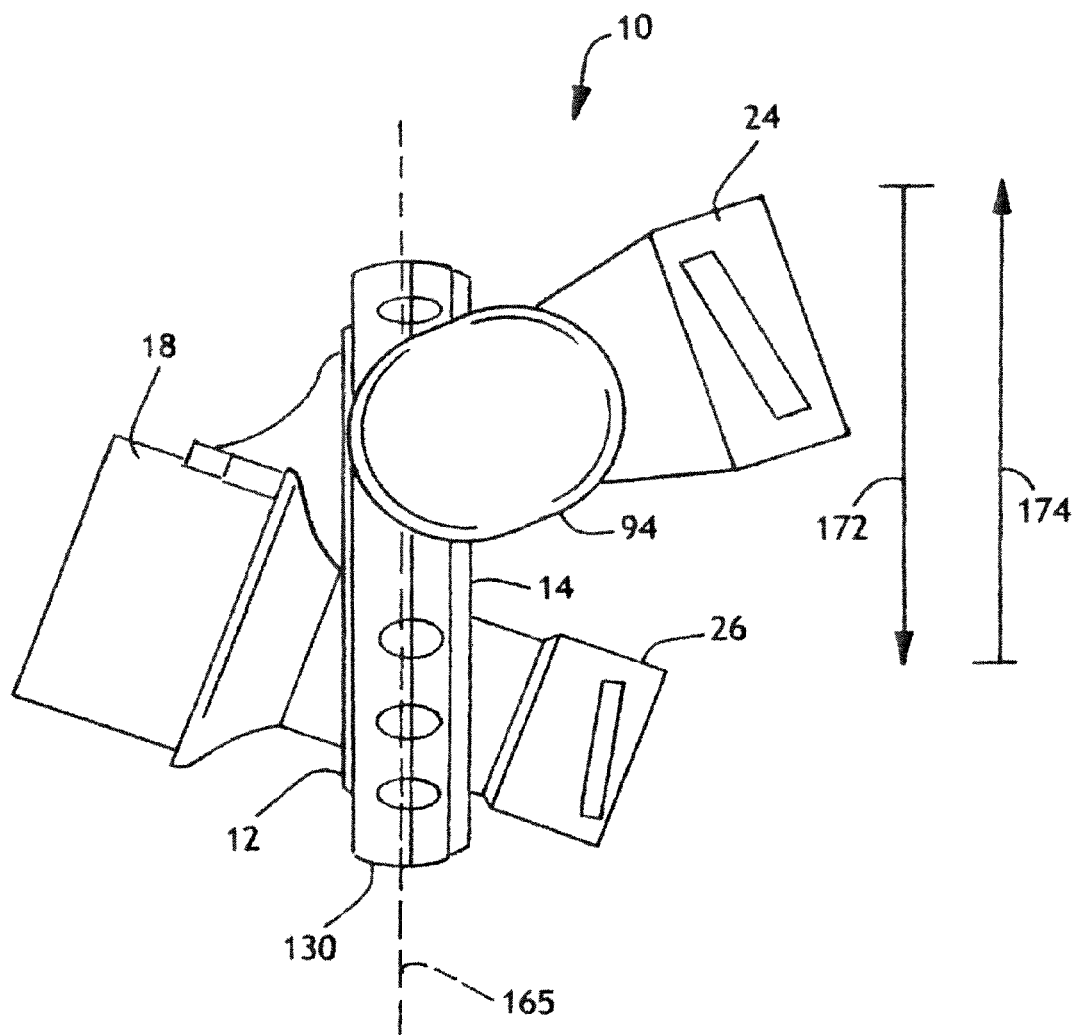
FIG. 13 is a side view of the respiratory access assembly of the present disclosure, showing the port of the distal disk positioned in an axial alignment with the second port of the proximal disk in an open position (second open position).

Turning now to the drawings, as illustrated in FIGS. 1-13, a rotating respiratory access port assembly 10 is provided. The assembly 10, as shown in FIGS. 1-3, 6-8, 10A-D, and 11-13, includes a distal disk or plate 12 and a proximal disk or plate 14 which are positioned next to each other in a stacked and axially aligned configuration. The distal disk or plate 12 includes at least one angled port 16 whose opening extends through an angled cuff 18 (FIGS. 1-3 and 8). The proximal disk or plate 14 includes a first angled port 20 and a second angled port 22 whose openings each extend through first and second angled cuffs 24, 26, respectively (FIGS. 1, 2, 4, 10A-D, 11-13). When the distal disk or plate 12 is moved or rotated, it provides a position which axially aligns its port 16 with the first port 20 of the proximal disk or plate 14 (FIG. 11). Alternatively, when the distal disk or plate 12 is moved or rotated it may also provide a position which axially aligns its port 16 with the second port 22 in the proximal disk or plate 14 (FIG. 13). In yet another alternative, when the distal disk or plate 12 is moved or rotated, it may also provide a position in which its port 16 is not aligned with either the first port 20 or the second port 22. In each instance, when one set of ports align axially, the opposite port on the proximal disk or plate 14 will be blocked by a portion of the distal disk or plate 12. In this position, the ports 16, 20 and 22 are blocked by a portion of one of the disks or plates 12 or 14 in a closed position and none are aligned (FIG. 12).

Figure 2:
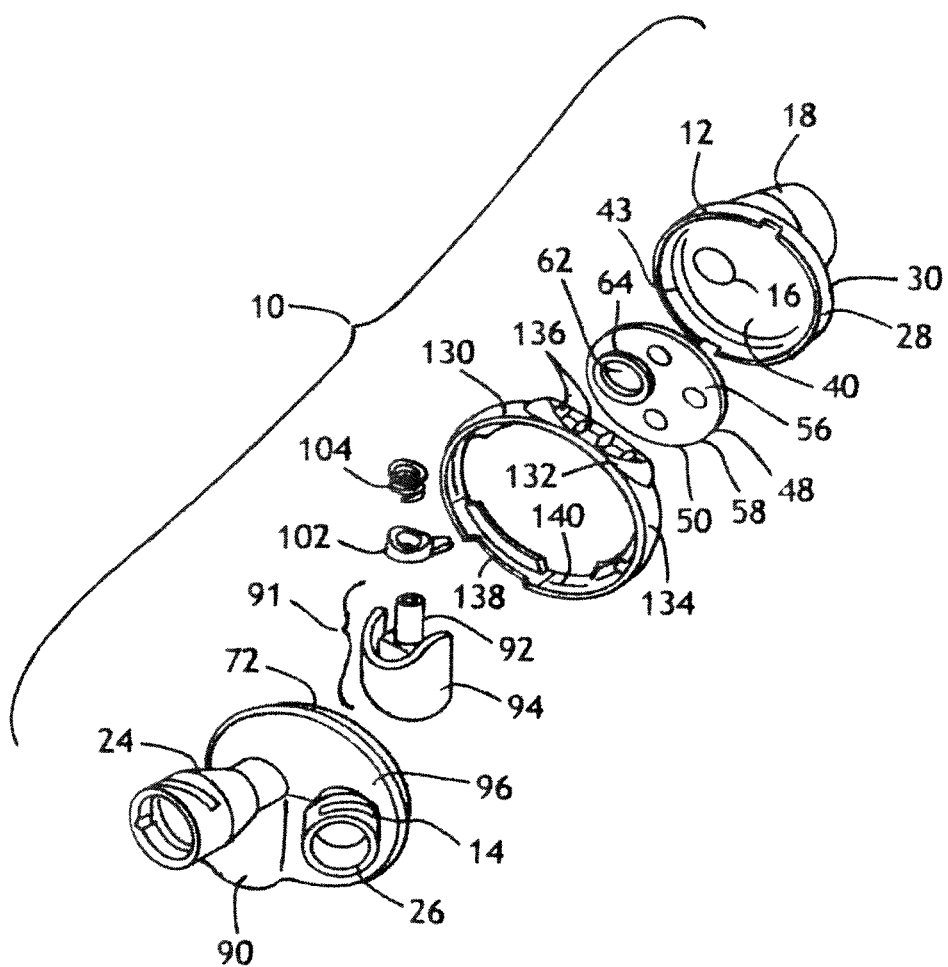
FIG. 2 is an exploded perspective view of the respiratory access assembly of FIG. 1.
Figure 3:
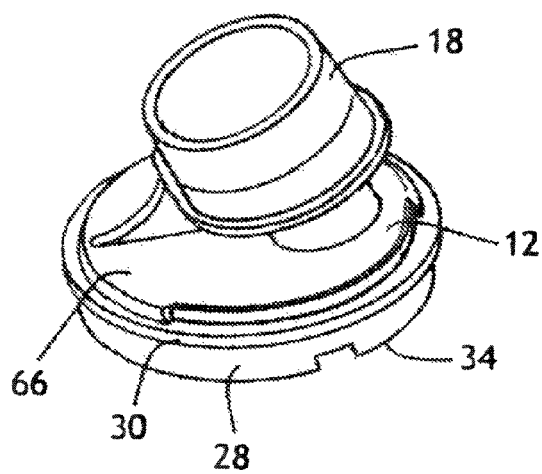
FIG. 3 is a perspective view of a distal disk of FIGS. 1 and 2.
Figure 8:
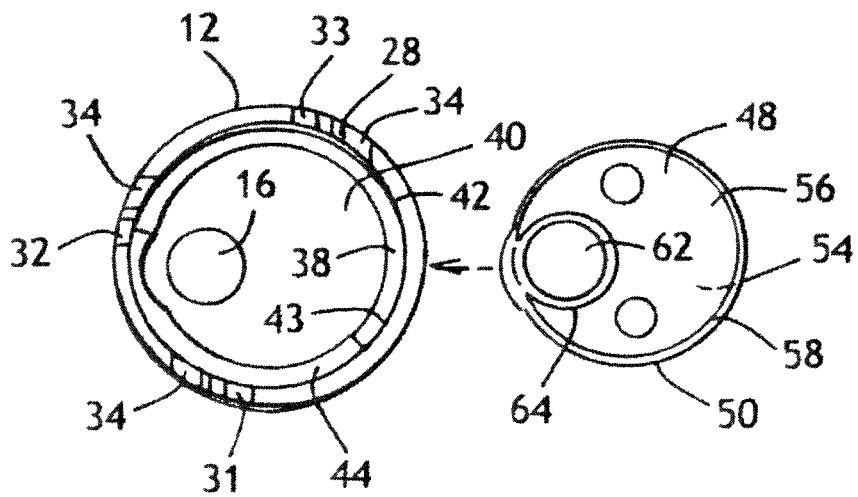
FIG. 8 is a plan view of a proximal surface of the distal disk of FIG. 3, and showing a seal which is desirably positioned on the proximal surface.
Figure 9A:
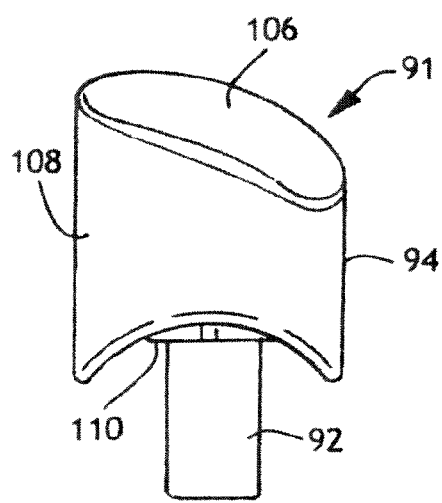
FIG. 9A is a proximal plan view of the button of FIGS. 1 and 2.
Figure 9B:
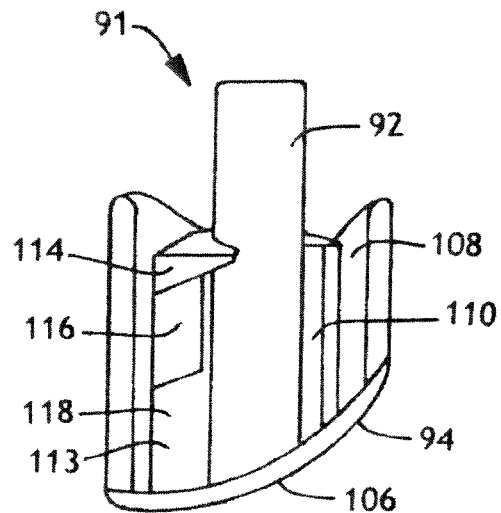
FIG. 9B is a distal plan view of the button of FIG. 9A.
Figure 9C:
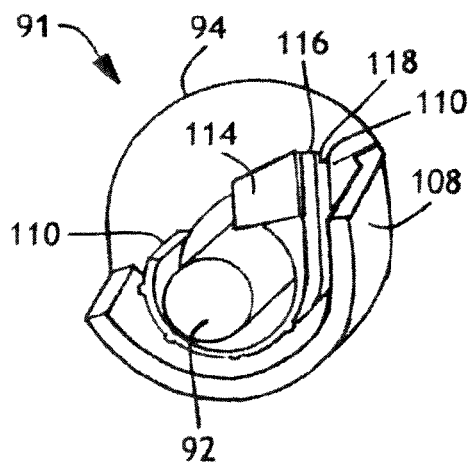
FIG. 9C is a side view of the button of FIGS. 9A and 9B.
Figure 9D:
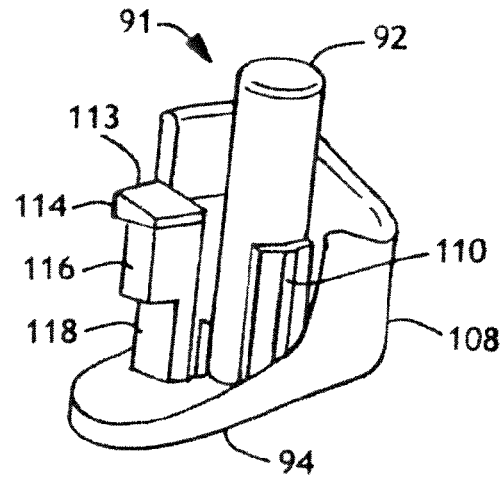
FIG. 9D is another side view of the button of FIGS. 9A-C.

The distal disk 12 also desirably includes a lip 28 positioned on an outer edge 30 of the disk 12, as illustrated in FIGS. 2, 3 and 8. The lip 28 may include three notches, that is, a first notch 31, a second notch 32 and a third notch 33 about the lip 28. The three notches, 31, 32 and 33 cooperate with other components to provide three predetermined positions in which the disks 12, 14 releaseably lock together. A plurality of ramps (collectively "34") may also be provided on the lip 28 adjacent each first, second and third notch 31, 32, and 33. The ramps 34 desirably provide mechanical stability and strength against bending forces. In addition, the ramps 34 may provide clearance for a spring and/or a plunger provided with a button, described in greater detail below. A groove 38 may desirably be provided on at least a portion of a proximal surface 40 of the distal disk 12 adjacent a junction 42 of the lip 28 and the edge 30 of the distal disk 12. The groove 38 desirably follows a portion of the inner periphery 43 of the distal disk 12. Alternatively, however, no groove may be formed in the disk 12 (not shown). A rib 44 is desirably provided, and it also extends around a portion of the inner periphery 43 of the distal disk 12. Alternatively, a pair of stop tabs may also be used in place of the rib (not shown). These components cooperate with components of the proximal disk 14, described in detail below, to permit rotation of the distal and proximal disks 12, 14. A flexible polymer elastomeric seal 48 is also desirably provided on the proximal surface 40 of the distal disk 12. The seal is used to maintain the closed ventilation system seal between the distal and the proximal disks 12, 14.

The seal 48, as shown in FIGS. 2 and 8, also is desirably disk-shaped, and it has a perimeter which is slightly smaller than a perimeter of the inner periphery 43 of the distal disk 12. The seal 48 is substantially flat on its distal surface 54, but on its proximal surface 56, the seal 48 has a perimeter rib 58 extending about its perimeter 50. Similarly, the seal 48 has an opening 62 formed therethrough which is configured, but not by way of limitation, to conform to the configuration of at least the port 16. Desirably, however, the opening 62 also at least substantially conforms to the first port 20 and the second port 22. A port rib 64 is formed about the opening 62 on the proximal surface 56 of the seal 48. The perimeter rib 58 and the port rib 64 cooperate with components on a distal surface 65 of the proximal disk 14 to create a seal therebetween, as will be described in detail below. It will be understood that when the seal 48 is positioned centrally on the proximal surface 40 of the distal disk 12, the perimeter rib 58, a portion of the proximal surface 40 of the distal disk 12 and its lip 28 may cooperate to provide the groove 38 (not shown).

The distal disk 12 includes the cuff 18 formed about the port 16 on a distal surface 66 thereof (FIG. 1-3). The cuff 18 desirably is configured to releaseably couple to a connector or a manifold 175 which is coupled to or forms a portion of an artificial airway. This connection may be made, for example, by frictional rotational, leur lock, interlocking tabs, threaded components, and so forth.

The proximal disk 14 (FIGS. 1, 2, 4, 6, 7 and 10A-D) includes a distal surface 68 and an outer edge 70. An outer lip 72 is formed adjacent or near the outer edge 70 and is configured to cooperatively overlap the lip 28 of the distal disk 12. The outer lip 72 has more than one notch, and desirably may include two notches (collectively "74") formed therein. An inner rib 76 is formed a short distance interiorly relative to the outer lip 72 on the distal surface 68 of the proximal disk 14. The inner rib 76 does not extend in a complete circle about an inner periphery 79 of the outer lip 72. The short distance defines a rotating groove 80 configured to accept the lip 28 of the distal disk 12. A tab 81 is provided on the inner rib 76 which acts a stop tab 81.

Figure 4:
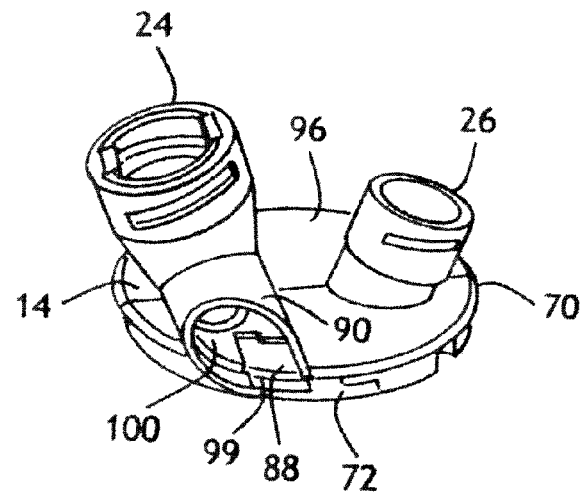
FIG. 4 is a perspective view of a proximal disk of FIGS. 1 and 2.
Figure 6:
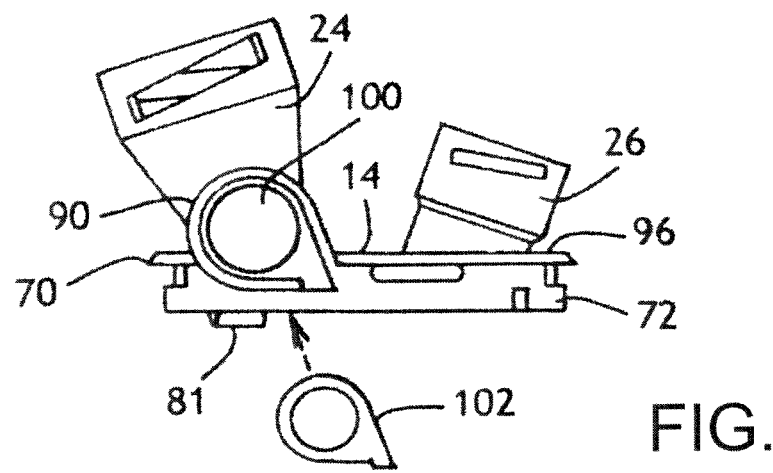
FIG. 6 is a side view of the proximal disk of FIG. 4 showing the O-ring separately.
Figure 7:
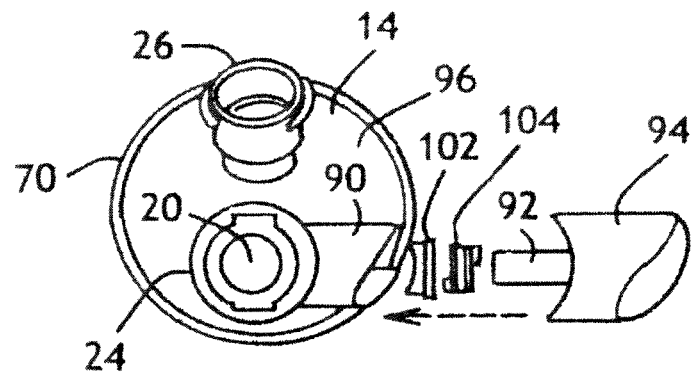
FIG. 7 is a plan view of a proximal surface of the proximal disk of FIGS. 6 and 7, showing a button, a spring and an O-ring.

In operation, the lip 28 of the distal disk 12 fits in the groove 80 in between the outer lip 72 and the inner rib 76 of the proximal disk 14 (FIGS. 8 and 10A-D). The tab 81 of the proximal disk 14 cooperatively fits within the groove 38 of the distal disk 12, thereby permitting the distal disk 12 to rotate within the confines of the groove 38 relative to the proximal disk 14. The rib 44 of the distal disk 12 also acts as a stop, thereby preventing continuous rotation of the distal disk 12. Further, these components prevent over-rotation which would likely result in kinking of any suction catheter position through the rotating access port 10. Turning back to the proximal disk 14, perimeter ribs 82, 83 are formed about the periphery of the first and second ports 20, 22. In between the first and second ports 20, 22, a generally D-shaped portion 84 is provided, and is used in providing a closed position, which will be described in further detail below. A channel 86 may be provided which connects and extends between the two perimeter ribs 82, 83. The channel permits the first and second ports 20, 22 to be in both gaseous and fluid communication with each other. However, it will be appreciated that the proximal disk 12 may be formed without a channel between the first and second ports 20, 22 as well (not shown). An opening 88 is formed through a portion of the rotating groove 80. The opening 88 extends into a button housing 90 and it is configured to at least partially contain an actuator or button assembly 91 including a blocking portion or plunger 92 and a button 94 (FIGS. 4, 6, 7 A-D and 10 A-D).

The button housing 90 is formed from a portion of a proximal surface 96 of the proximal disk 14. The proximal surface 96 includes first and second cuffs 24, 26 which surround the first and second ports 20, 22, respectively. Each first and second port 20, 22 and its respective first and second cuff 24, 26 are provided, as noted previously, at an angle relative to the stacked distal and proximal disks 12, 14.

At least a portion of the button housing 90 may be formed to intersect the first cuff 24 of the first port 20 at about a 90 degree angle. The housing 90 may be formed, for example, semi-cylindrically (that is, for example, but not by way of limitation, generally C-shaped or U-shaped) to accommodate the configuration of the button assembly 91 and the button 94 and plunger 92 integrally formed therewith or coupled thereto (FIGS. 4, 6, 7 and 10 A-D). The button housing 90 is also desirably formed to include a side opening 100 having a flange 101 in a portion of the outer lip 72 of the proximal disk 14, which also is in an open communication with the opening formed through the first cuff 22. The proximal disk 14 includes a notch or divot 99 in the outer lip 72; a portion of the button 94 contacts the divot 99 in order to hold the button 94 to the distal and proximal disks 12, 14. The divot 99 is formed to communicate with the side opening 100 in the first cuff 24 of the first port 20.

A flexible, polymer elastomeric O-ring 102 is desirably positioned next to an inner perimeter of the side opening 100. The O-ring 102 provides a seal for the plunger against PEEP pressure loss and a landing area for a spring 104 which may desirably be constructed of metal, plastic, or any combination thereof. The spring 104 is positioned over the plunger 92 and extends between the O-ring 102 and the button 94, biasing the button 94 and plunger 92 outward. The spring 104 comprises a coiled spring, however, other non-coiled springs and biasing devices may be used.

It has been surprisingly found that inserting an O-ring 102 into the inner perimeter of the side opening 100 is quite time consuming and labor intensive. It has also been found that an O-ring inserted in such a manner can become loose during assembly of the completed device and, even if seemingly in its proper place, can be a source of pressure loss. As a result of these difficulties, it has been found that an over-molded O-ring, formed in place in the inner perimeter of the side opening, can more effectively seal against leakage while retaining its position during assembly.

In order to produce the over-molded O-ring 102 in place, the proximal disk 14 is first formed from one or more polymers. Examples of these materials include, but are not limited to, polycarbonate, acrylic, and so forth. When the proximal disk 14 is formed, a small channel 85 (on the order of a few millimeters or less in diameter) is included, extending from one of the surfaces of the disk 14 to an inner perimeter of the opening 100 (FIG. 10B). An insert that mimics the dimensions and location of the plunger 92 is positioned in the side opening 100, thus creating a void space that matches the desired dimensions of the O-ring 102. The insert also includes a vent for air and gases to escape during the molding process but which does not allow molten polymer to pass through it. An elastomeric polymer is injected through the channel to fill the void space and create the O-ring 102 in place. Should further assurance of non-leakage be desired, additional O-rings may be manually inserted between the over-molded O-ring 102 and the button 94, though this is not generally necessary.

The selection of polycarbonate as the substrate material from which the proximal disk 14 is made and the selection of a thermoplastic elastomer that adheres well to polycarbonate for the O-ring 102 helps ensure that the O-ring 102 will remain attached to the proximal disk 14 prior to and during assembly of the manifold and that leakage will be minimal or non-existent upon final assembly. In general, any thermoplastic elastomer may be used as long as it is sufficiently stable in use, adheres to the substrate (e.g. polycarbonate) and can function as an O-ring. A particularly suitable thermoplastic elastomer has been found to be VERSAFLEX® 1040-X OM from GLS Corp. in McHenry, Ill. The substrate can be a number of polymers, though polycarbonate, as noted above, performs well. Other polymers such as acrylic, ABS, and XYDAR® liquid crystal polymers also function sufficiently. A particularly well suited polycarbonate is a LEXAN® material sold under the designation Sabic HPS2R by Sabic Innovative Plastics Holdings BV.

Figure 5A:
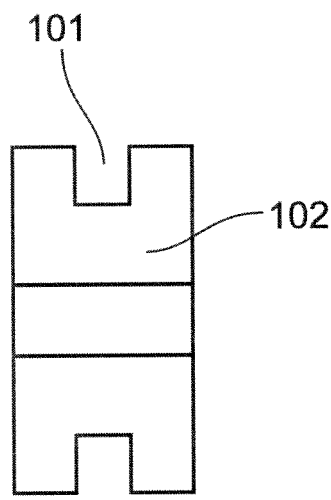
FIG. 5A is a side view of an O-ring formed around a flange in the opening, illustrating its 'H" shape.
Figure 5B:
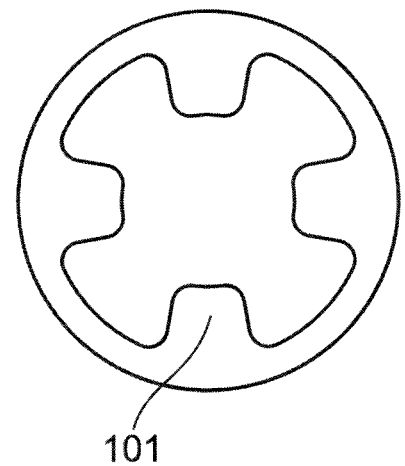
FIG. 5B is a top view of a flange in the opening, around which an O-ring may be formed.

The O-ring 102 is desirably formed around both sides of the flange 101 in the side opening 100. The forming of the O-ring in this shape helps to keep the O-ring in place, as even an over-molded O-ring can come loose under extreme conditions if it is only attached on one side of the flange. A side or cross-sectional view of the O-ring 102 on the flange 101 reveals that it is "H" shaped if formed on both sides of the flange 101 (FIG. 5A). In addition, the flange 101 need not be perfectly circular. FIG. 5B illustrates a flange that provides greater surface area for the O-ring to adhere to while providing a stable platform for the spring. This "clover leaf" flange shape allows the spring to rest on the flange foundation but helps keep the O-ring from pushing out of place when the button is depressed. Other shapes may of course be used.

The button 94, as illustrated in FIGS. 9A-D, may also desirably include a thumb landing area 106 and an outer shell 108 which substantially follows the configuration of the button housing 90, and which is therefore generally C-shaped or U-shaped. The button 94 also includes an inner shell 110 of similar C or U-shaped configuration which is spaced a short distance from the outer shell 108. The plunger 92 is coupled to an inner surface (not shown) of the thumb landing area 106 and it is positioned a short distance away from the inner shell 110. The button housing 90 is desirably stacked or positioned between the respective outer and inner shells 108, 110 in order to hold the plunger 94 in a position to extend from the housing 90 into the side opening 100, thereby blocking the first port 22 in its first cuff 24 (FIGS. 7 and 10A-D). In addition, the perimeter edge 113 of the inner shell 110 includes a holding tab 114, a locking tab 116, and a movement-permitting portion 118, which operates to permit movement of the button 92 and the plunger 94 in order to both move and releaseably lock the button and plunger 94 in a plurality of predetermined positions.

The holding tab 14 is configured to hold the button 94 in a coupled position against the distal and proximal disks 12, 14 (FIGS. (A-D and 10A-D). The holding tab 14 contacts the lip 28 of the distal disk 12, and will not permit the button 94 to move away from the stacked disks 12, 14, even though the spring 104 biases the button 94 outward, away from the disks 12, 14. The locking tab 116 is configured to fit within and contact each of the first, second and third notches 31, 32, or 33, respectively, on the lip 28 of the rotary disk 12. When the locking tab 116 is positioned to contact the lip 28 via the notches 31, 32, or 33, the locking tab 116 locks or prevents rotation of the distal disk 12 relative to the proximal disk 14. The movement-permitting portion 118 is configured to extend below the lip 28 of the distal disk 12. In this position, the locking tab 116 is positioned against the inner periphery 43 of the distal disk 12. Therefore, the locking tab 116 is disengaged and un-locked from the distal disk 12, permitting the distal disk 12 to rotate within the confines previously described (i.e. about 180 degrees or less) of the proximal disk 14. The movement-permitting portion 118 only permits movement when a user depresses the button 94 inward, toward the disks 12, 14 and holds the button 94 in the depressed position while starting the rotation of the distal disk 12. In this manner, the locking tab 116 is positioned in the locked position and the blocking portion or plunger 92 is extended via the side opening 100 into the first cuff 24 of the first port 20, thereby effectively blocking the first port 20 and preventing the passage of a suction catheter therethrough. The plunger 92 remains in the first port 20 until the distal disk 12 is rotated such that one of the first, second and third notches 31, 32, and/or 33 crosses the movement-permitting portion 118. The first, second or third notches 31, 32, or 33 provide sufficient space to permit the outward movement of the perimeter edge 113, thereby permitting outward movement of the spring-biased plunger 92 and button 94 away from the outer edges 30, 70 of the distal and proximal disks 12, 14 such that the locking tab 116 is moved outward into a position in one of the notches 31, 32, or 33 to block the rotation of the distal disk 12 and thereby lock the distal disk 12 into a fixed, non-moveable position. In this position, the plunger 92 is again positioned away from the opening through the first port 20 and/or first cuff 24, and it moves back into the button housing 90 thereby un-blocking the first port 20.

The distal disk 12, its seal 48, the proximal disk 14, the spring 104, the O-ring 102 as well as the button assembly 91 cooperate together to define three predetermined positions of the assembly 10. The first position, as shown in FIG. 11, defines an opened position (a first open position) of the port 16 and cuff 18 aligned with the first port 20 and first cuff 24, such that an axial alignment and communication is created through the aligned ports 16, 20 and cuffs 18, 24, respectively. The seal 48 and its respective ribs 58, 64 positioned on the distal disk 12 act to seal and maintain the secretions substantially within the assembly 10 and the closed circuit ventilation system such that PEEP may be maintained. In the first position, the seal 48 and the proximal surface 40 of the distal disk 12 also provide a closure to the second port 22, which may also have a cap (not shown) which provides a closure to the cuff 26.

The second position, as illustrated in FIG. 12, defines a closed position of the port 16 relative to the first and second ports 20, 22, in that the distal disk 12 is rotated to a position between first and second ports 20 and 22. The seal 48 then assists in sealing all ports 16, 20, 22 closed. Notably, in this position, the port 16 and its cuff 18 of the distal disk 12 are out of an axial alignment with either the first port 20 or the second port 22. The first and/or second cuffs 24, 26 may also have a cap (not shown) to provide a closure over each cuff 24, 26. Alternatively, one cuff 24 or 26 may have a suction catheter assembly or other device coupled thereto which provides a closure.

The third position, as shown in FIG. 13, defines an opened position (a second open position) of the port 16 and cuff 18 of the distal disk in axial alignment with the second port 22 and second cuff 26 of the proximal disk 14. In this position, an axial alignment and operable communication is created through the ports 16, 22 and cuffs 18, 26. The seal 48 and its respective ribs 58, 64 positioned on the distal disk 12 acts to seal and maintain the secretions substantially within the assembly 10 and the closed circuit ventilation system such that PEEP may be maintained. In this third position (second open position), the seal 48 and the proximal surface 40 of the distal disk 12 also provide a closure to the first port 20, which may also have a cap for closure (not shown) or an attached suction catheter assembly or other device (not shown) which acts to provide a closure.

While the present disclosure has been described in connection with certain preferred embodiments it is to be understood that the subject matter encompassed by way of the present disclosure is not to be limited to those specific embodiments. On the contrary, it is intended for the subject matter of the disclosure to include all alternatives, modifications and equivalents as can be included within the spirit and scope of the following claims.

What is claimed is:

1. A respiratory access assembly, comprising:
   a distal plate having a port, the port adapted to be positioned in operable communication with an artificial airway of a patient;
   a proximal plate including a first port and a second port, the distal plate positioned against the proximal plate in a stacked configuration, each plate configured to move; and
   an actuator positioned adjacent to at least one plate, the actuator cooperating with at least one plate to permit movement of at least one plate when the actuator is positioned in a movement-enabling position, the actuator cooperating with both plates to lock the plates in a fixed position when the actuator is positioned in a locked position, such that the plates are locked into a predetermined position relative to each other, the actuator including a blocking portion which is configured to extend into at least one port when the actuator is positioned in the movement-enabling position, and to withdraw from the one port when the actuator is positioned in the locked position;
   wherein said blocking portion moves slidably within an O-ring which prevents loss of pressure around said blocking portion from said artificial airway, said O-ring being made by injection molding.

2. The respiratory access assembly of claim 1, wherein said O-ring is made from a thermoplastic elastomer and the plates are made from polycarbonate.

3. The respiratory access assembly of claim 1, wherein said proximal plate has a channel for the injection of a thermoplastic elastomer forming said O-ring in place.

* * * * *